(12) United States Patent
Toellner et al.

(10) Patent No.: US 10,589,012 B2
(45) Date of Patent: Mar. 17, 2020

(54) BLOOD PUMP FOR THE INVASIVE APPLICATION WITHIN A BODY OF A PATIENT

(71) Applicant: ECP ENTWICKLUNGSGESELLSCHAFT MBH, Berlin (DE)

(72) Inventors: Thomas Toellner, Berlin (DE); Mario Scheckel, Berlin (DE)

(73) Assignee: ECP ENTWICKLUNGSGESELLSCHAFT MBH, BerlinAmtsgericht Berlin (Charlottenburg) (DE)

( * ) Notice: Subject to any disclaimer, the term of this patent is extended or adjusted under 35 U.S.C. 154(b) by 0 days.

(21) Appl. No.: 15/815,931

(22) Filed: Nov. 17, 2017

(65) Prior Publication Data

US 2018/0133381 A1    May 17, 2018

Related U.S. Application Data

(63) Continuation of application No. 13/261,563, filed as application No. PCT/EP2011/003438 on Jul. 1, 2011, now Pat. No. 9,895,475.
(Continued)

(30) Foreign Application Priority Data

Jul. 15, 2010 (EP) .................................... 10075304

(51) Int. Cl.
*A61M 1/10* (2006.01)
*A61M 1/12* (2006.01)
(Continued)

(52) U.S. Cl.
CPC ............ *A61M 1/12* (2013.01); *A61M 1/1024* (2014.02); *A61F 2/82* (2013.01); *A61F 2/88* (2013.01);
(Continued)

(58) Field of Classification Search
CPC ....................................................... A61M 1/10
See application file for complete search history.

(56) References Cited

U.S. PATENT DOCUMENTS 3,510,229 A   5/1970   Smith et al.
3,568,659 A   3/1971   Karnegis
(Continued)

FOREIGN PATENT DOCUMENTS

CA   1008330 A    4/1977
CA   2311977 A1   12/2000
(Continued)

OTHER PUBLICATIONS

International Search Report for PCT/EP2011/0034388, dated May 15, 2011 (6 pages).

*Primary Examiner* — Matthew W Schall
(74) *Attorney, Agent, or Firm* — White & Case LLP

(57) ABSTRACT

The invention relates to a blood pump for the invasive application within a body of a patient comprising a rotor (43, 27) which is drivable about an axis of rotation and is radially compressible or expandable and which has a hub (18, 28) and at least one impeller blade (14, 15, 16, 17, 29, 30) fastened thereto, as well as comprising a housing (19, 19') which is compressible or expandable in the radial direction by an axial stretching or axial compression. The object of making both the rotor and the housing expandable and compressible in as simple a manner as possible is achieved in accordance with the invention in that a control body (21) is provided which passes through the hub (18) in the
(Continued)

Figure 1:
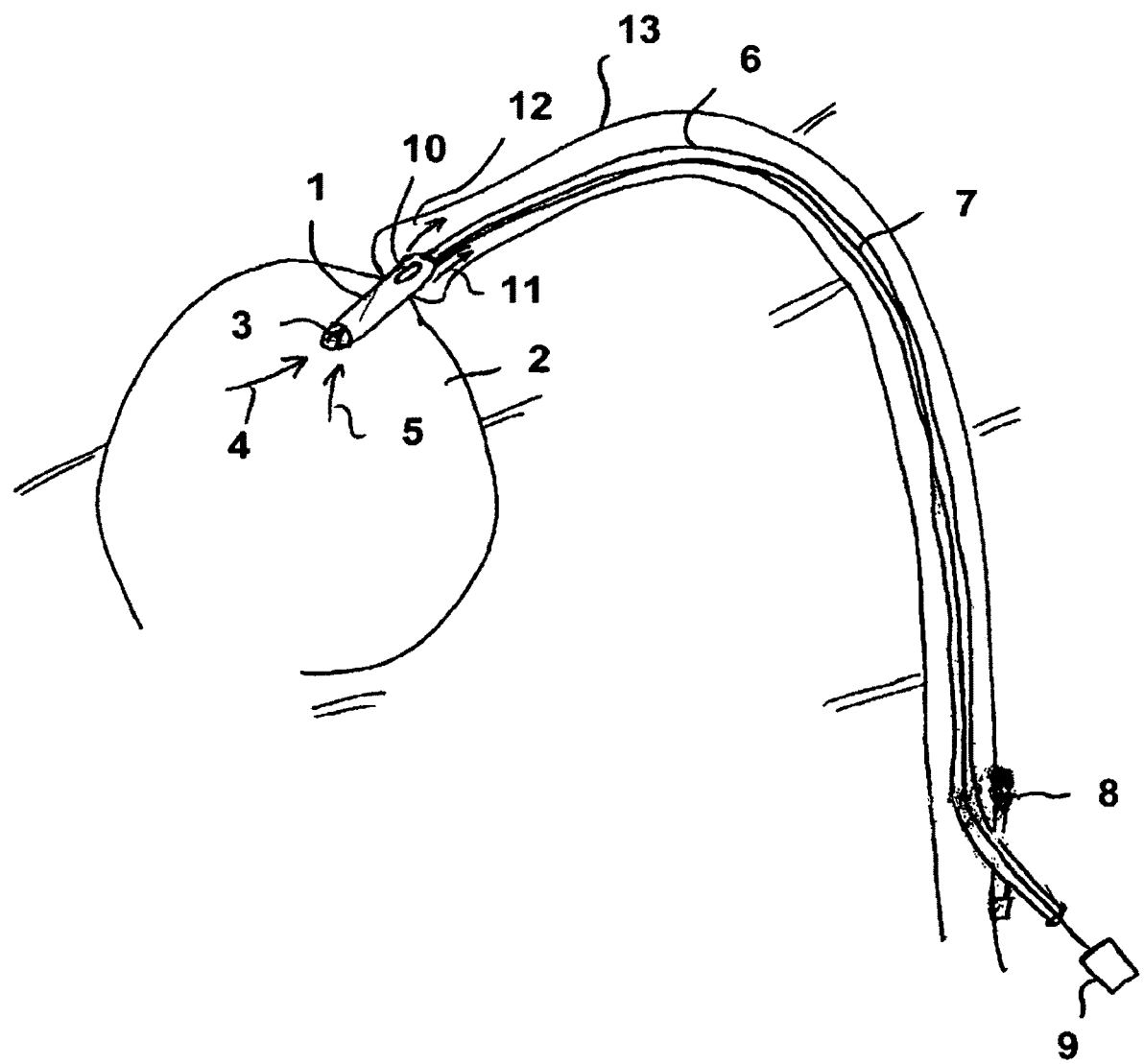

longitudinal direction, which is freely axially displaceable relative to the hub and which is coupled to the housing on the distal side of the rotor such that it exerts pulling and/or compression forces on the housing by a movement in the longitudinal direction with respect to the housing.

21 Claims, 4 Drawing Sheets

Related U.S. Application Data

(60) Provisional application No. 61/364,595, filed on Jul. 15, 2010.

(51) Int. Cl.
    *A61F 2/82*  (2013.01)
    *A61F 2/88*  (2006.01)

(52) U.S. Cl.
    CPC ............... *A61M 1/10* (2013.01); *A61M 1/101* (2013.01); *A61M 1/1012* (2014.02); *A61M 1/1034* (2014.02); *A61M 1/122* (2014.02); *A61M 1/125* (2014.02); *A61M 2205/02* (2013.01); *A61M 2205/04* (2013.01); *A61M 2210/12* (2013.01)

(56) References Cited

U.S. PATENT DOCUMENTS

| | | |
|---|---|---|
| 3,802,551 A | 4/1974 | Somers |
| 3,812,812 A | 5/1974 | Hurwitz |
| 4,014,317 A | 3/1977 | Bruno |
| 4,207,028 A | 6/1980 | Ridder |
| 4,559,951 A | 12/1985 | Dahl et al. |
| 4,563,181 A | 1/1986 | Wijayarathna et al. |
| 4,679,558 A | 7/1987 | Kensey et al. |
| 4,686,982 A | 8/1987 | Nash |
| 4,747,821 A | 5/1988 | Kensey et al. |
| 4,749,376 A | 6/1988 | Kensey et al. |
| 4,753,221 A | 6/1988 | Kensey et al. |
| 4,801,243 A | 1/1989 | Norton |
| 4,817,613 A | 4/1989 | Jaraczewski et al. |
| 4,919,647 A | 4/1990 | Nash |
| 4,957,504 A | 9/1990 | Chardack |
| 4,969,865 A | 11/1990 | Hwang et al. |
| 4,995,857 A | 2/1991 | Arnold |
| 5,011,469 A | 4/1991 | Buckberg et al. |
| 5,040,944 A | 8/1991 | Cook |
| 5,042,984 A | 8/1991 | Kensey et al. |
| 5,052,404 A | 10/1991 | Hodgson |
| 5,061,256 A | 10/1991 | Wampler |
| 5,092,844 A | 3/1992 | Schwartz et al. |
| 5,097,849 A | 3/1992 | Kensey et al. |
| 5,108,411 A | 4/1992 | McKenzie |
| 5,112,292 A | 5/1992 | Hwang et al. |
| 5,113,872 A | 5/1992 | Jahrmarkt et al. |
| 5,117,838 A | 6/1992 | Palmer et al. |
| 5,118,264 A | 6/1992 | Smith |
| 5,145,333 A | 9/1992 | Smith |
| 5,163,910 A | 11/1992 | Schwartz et al. |
| 5,169,378 A | 12/1992 | Figuera |
| 5,183,384 A | 2/1993 | Trumbly |
| 5,191,888 A | 3/1993 | Palmer et al. |
| 5,201,679 A | 4/1993 | Velte, Jr. et al. |
| 5,250,059 A | 10/1993 | Andreas et al. |
| 5,275,580 A | 1/1994 | Yamazaki |
| 5,373,619 A | 12/1994 | Fleischhacker et al. |
| 5,376,114 A | 12/1994 | Jarvik |
| 5,501,574 A | 3/1996 | Raible |
| 5,531,789 A | 7/1996 | Yamazaki et al. |
| 5,701,911 A | 12/1997 | Sasamine et al. |
| 5,749,855 A | 5/1998 | Reitan |
| 5,755,784 A | 5/1998 | Jarvik |
| 5,776,190 A | 7/1998 | Jarvik |
| 5,813,405 A | 9/1998 | Montano, Jr. et al. |
| 5,820,571 A | 10/1998 | Erades et al. |
| 5,851,174 A | 12/1998 | Jarvik et al. |
| 5,882,329 A | 3/1999 | Patterson et al. |
| 5,888,241 A | 3/1999 | Jarvik |
| 5,938,672 A | 8/1999 | Nash |
| 6,001,078 A | 12/1999 | Reekers |
| 6,030,397 A | 2/2000 | Monetti et al. |
| 6,129,704 A | 10/2000 | Forman et al. |
| 6,152,693 A | 11/2000 | Olsen et al. |
| 6,168,624 B1 | 1/2001 | Sudai |
| 6,193,922 B1 | 2/2001 | Ederer |
| 6,254,359 B1 | 7/2001 | Aber |
| 6,302,910 B1 | 10/2001 | Yamazaki et al. |
| 6,308,632 B1 | 10/2001 | Shaffer |
| 6,336,939 B1 | 1/2002 | Yamazaki et al. |
| 6,346,120 B1 | 2/2002 | Yamazaki et al. |
| 6,387,125 B1 | 5/2002 | Yamazaki et al. |
| 6,503,224 B1 | 1/2003 | Forman et al. |
| 6,506,025 B1 | 1/2003 | Gharib |
| 6,508,787 B2 | 1/2003 | Erbel et al. |
| 6,517,315 B2 | 2/2003 | Belady |
| 6,527,521 B2 | 3/2003 | Noda |
| 6,533,716 B1 | 3/2003 | Schmitz-Rode et al. |
| 6,537,030 B1 | 3/2003 | Garrison |
| 6,537,315 B2 | 3/2003 | Yamazaki et al. |
| 6,592,612 B1 | 7/2003 | Samson et al. |
| 6,652,548 B2 | 11/2003 | Evans et al. |
| 6,652,576 B1 | 11/2003 | Stalker |
| 6,719,791 B1 | 4/2004 | Nusser et al. |
| 6,860,713 B2 | 3/2005 | Hoover |
| 6,945,977 B2 | 9/2005 | Demarais et al. |
| 6,981,942 B2 | 1/2006 | Khaw et al. |
| 7,022,100 B1 | 4/2006 | Aboul-Hosn et al. |
| 7,027,875 B2 | 4/2006 | Siess et al. |
| 7,074,018 B2 | 7/2006 | Chang |
| 7,179,273 B1 | 2/2007 | Palmer et al. |
| 7,393,181 B2 | 7/2008 | McBride et al. |
| 7,467,929 B2 | 12/2008 | Nusser et al. |
| 7,731,675 B2 | 6/2010 | Aboul-Hosn et al. |
| 7,841,976 B2 | 11/2010 | McBride et al. |
| 7,878,967 B1 | 2/2011 | Khanal |
| 7,927,068 B2 | 4/2011 | McBride et al. |
| 7,934,909 B2 | 5/2011 | Nuesser et al. |
| 8,690,749 B1 | 4/2014 | Nunez |
| 2002/0123661 A1 | 9/2002 | Verkerke et al. |
| 2003/0135086 A1 | 7/2003 | Khaw et al. |
| 2003/0231959 A1 | 12/2003 | Snider |
| 2004/0044266 A1 | 3/2004 | Siess et al. |
| 2004/0046466 A1 | 3/2004 | Siess et al. |
| 2004/0093074 A1 | 5/2004 | Hildebrand et al. |
| 2004/0098110 A1 | 5/2004 | Williams et al. |
| 2004/0215222 A1 | 10/2004 | Krivoruchko |
| 2004/0215228 A1 | 10/2004 | Simpson et al. |
| 2006/0008349 A1 | 1/2006 | Khaw |
| 2006/0062672 A1 | 3/2006 | McBride et al. |
| 2006/0195004 A1 | 8/2006 | Jarvik |
| 2008/0132747 A1 | 6/2008 | Shifflette |
| 2008/0262584 A1 | 10/2008 | Bottomley et al. |
| 2008/0306327 A1 | 12/2008 | Shifflette |
| 2009/0060743 A1 | 3/2009 | McBride et al. |
| 2009/0062597 A1 | 3/2009 | Shifflette |
| 2009/0093764 A1 | 4/2009 | Pfeffer et al. |
| 2009/0093796 A1 | 4/2009 | Pfeffer et al. |
| 2010/0041939 A1 | 2/2010 | Siess |
| 2010/0268017 A1 | 10/2010 | Siess |
| 2011/0004046 A1 | 1/2011 | Campbell et al. |
| 2011/0238172 A1 | 9/2011 | Akdis |
| 2011/0257462 A1 | 10/2011 | Rodefeld et al. |
| 2011/0275884 A1 | 11/2011 | Scheckel |
| 2012/0039711 A1 | 2/2012 | Roehn |
| 2012/0041254 A1 | 2/2012 | Scheckel |
| 2012/0046648 A1 | 2/2012 | Scheckel |
| 2012/0093628 A1 | 4/2012 | Liebing |
| 2012/0101455 A1 | 4/2012 | Liebing |
| 2012/0142994 A1 | 6/2012 | Toellner |
| 2012/0179247 A1 | 7/2012 | Navia |
| 2012/0184803 A1 | 7/2012 | Simon et al. |

(56) References Cited

U.S. PATENT DOCUMENTS

| | | |
|---|---|---|
| 2012/0224970 A1 | 9/2012 | Schumacher et al. |
| 2012/0234411 A1 | 9/2012 | Scheckel |
| 2012/0237353 A1 | 9/2012 | Schumacher et al. |
| 2012/0237357 A1 | 9/2012 | Schumacher et al. |
| 2012/0264523 A1 | 10/2012 | Liebing |
| 2012/0265002 A1 | 10/2012 | Roehn et al. |
| 2012/0294727 A1 | 11/2012 | Roehn |
| 2012/0301318 A1 | 11/2012 | Er |
| 2012/0308406 A1 | 12/2012 | Schumacher |
| 2013/0019968 A1 | 1/2013 | Liebing |
| 2013/0041202 A1 | 2/2013 | Toellner |
| 2013/0060077 A1 | 3/2013 | Liebing |
| 2013/0066139 A1 | 3/2013 | Wiessler et al. |
| 2013/0085318 A1 | 4/2013 | Toellner |
| 2013/0177409 A1 | 7/2013 | Schumacher et al. |
| 2013/0177432 A1 | 7/2013 | Toellner et al. |
| 2013/0204362 A1 | 8/2013 | Toellner et al. |
| 2013/0237744 A1 | 9/2013 | Pfeffer et al. |
| 2014/0039465 A1 | 2/2014 | Schulz et al. |

FOREIGN PATENT DOCUMENTS

| | | |
|---|---|---|
| CA | 2701809 A1 | 4/2009 |
| CA | 2701810 A1 | 4/2009 |
| DE | 2207296 | 8/1972 |
| DE | 2113986 | 9/1972 |
| DE | 2233293 | 1/1973 |
| DE | 2613696 | 10/1977 |
| DE | 4124299 | 1/1992 |
| DE | 69103295 | 12/1994 |
| DE | 69017784 | 11/1995 |
| DE | 19535781 | 3/1997 |
| DE | 19711935 | 4/1998 |
| DE | 29804046 | 4/1998 |
| DE | 69407869 | 4/1998 |
| DE | 69427390 | 9/2001 |
| DE | 10059714 C1 | 5/2002 |
| DE | 10108810 A1 | 8/2002 |
| DE | 10155011 | 5/2003 |
| DE | 69431204 | 8/2003 |
| DE | 10336902 | 8/2004 |
| DE | 102005039950 | 3/2007 |
| DE | 102006031273 | 1/2008 |
| DE | 102010011998 | 9/2010 |
| EP | 480102 A1 | 4/1992 |
| EP | 560000 A1 | 9/1993 |
| EP | 629412 A1 | 12/1994 |
| EP | 768091 A1 | 4/1997 |
| EP | 884064 A1 | 12/1998 |
| EP | 0914171 A1 | 5/1999 |
| EP | 0916359 A1 | 5/1999 |
| EP | 951302 A1 | 10/1999 |
| EP | 1019117 A1 | 7/2000 |
| EP | 1066851 A1 | 1/2001 |
| EP | 1114648 A2 | 7/2001 |
| EP | 1337288 A1 | 8/2003 |
| EP | 1651290 A1 | 5/2006 |
| EP | 2218469 A1 | 8/2010 |
| EP | 2229965 A1 | 9/2010 |
| EP | 2301598 A1 | 3/2011 |
| EP | 2308524 A1 | 4/2011 |
| EP | 2343091 A1 | 7/2011 |
| EP | 2345440 A1 | 7/2011 |
| EP | 2366412 A2 | 9/2011 |
| EP | 2497521 A1 | 9/2012 |
| EP | 2606919 A1 | 6/2013 |
| EP | 2606920 A1 | 6/2013 |
| EP | 2607712 A1 | 6/2013 |
| GB | 2239675 | 7/1991 |
| RU | 2229899 | 6/2004 |
| WO | WO-9202263 A1 | 2/1992 |
| WO | WO-9302732 A1 | 2/1993 |
| WO | WO-9303786 A1 | 3/1993 |
| WO | WO-9314805 A1 | 8/1993 |
| WO | WO-94001148 A1 | 1/1994 |
| WO | WO-9405347 A1 | 3/1994 |
| WO | WO-9409835 A1 | 5/1994 |
| WO | WO-9420165 A2 | 9/1994 |
| WO | WO-9523000 A2 | 8/1995 |
| WO | WO-9618358 A1 | 6/1996 |
| WO | WO-9625969 A2 | 8/1996 |
| WO | WO-9744071 A1 | 11/1997 |
| WO | WO-9853864 A1 | 12/1998 |
| WO | WO-9919017 A1 | 4/1999 |
| WO | WO-0027446 | 5/2000 |
| WO | WO-0043054 | 7/2000 |
| WO | WO-0062842 | 10/2000 |
| WO | WO-2001007760 A1 | 2/2001 |
| WO | WO-2001007787 A1 | 2/2001 |
| WO | WO-2001083016 A2 | 11/2001 |
| WO | WO-2003057013 A2 | 7/2003 |
| WO | WO-2003103745 A2 | 12/2003 |
| WO | WO-2005002646 A1 | 1/2005 |
| WO | WO-2005016416 A1 | 2/2005 |
| WO | WO-2005021078 A1 | 3/2005 |
| WO | WO-2005030316 A1 | 4/2005 |
| WO | WO-2005032620 A1 | 4/2005 |
| WO | WO-2005081681 A2 | 9/2005 |
| WO | WO-2006020942 A1 | 2/2006 |
| WO | WO-2006034158 A2 | 3/2006 |
| WO | WO-2006133209 A1 | 12/2006 |
| WO | WO-2007003351 A1 | 1/2007 |
| WO | WO-2007103390 A2 | 9/2007 |
| WO | WO-2007103464 A2 | 9/2007 |
| WO | WO-2007112033 A2 | 10/2007 |
| WO | WO-2008017289 A2 | 2/2008 |
| WO | WO-2008034068 A2 | 3/2008 |
| WO | WO-2008054699 A2 | 5/2008 |
| WO | WO-2008106103 A2 | 9/2008 |
| WO | WO-2008116765 A2 | 10/2008 |
| WO | WO-2008124696 A1 | 10/2008 |
| WO | WO-2008137352 A1 | 11/2008 |
| WO | WO-2008137353 A1 | 11/2008 |
| WO | WO-2009015784 A1 | 2/2009 |
| WO | WO-2010042546 A1 | 4/2010 |
| WO | WO-2010133567 A1 | 11/2010 |
| WO | WO-2013034547 A1 | 3/2013 |
| WO | WO-2013092971 A1 | 6/2013 |
| WO | WO-2013093001 A2 | 6/2013 |
| WO | WO-2013093058 A1 | 6/2013 |

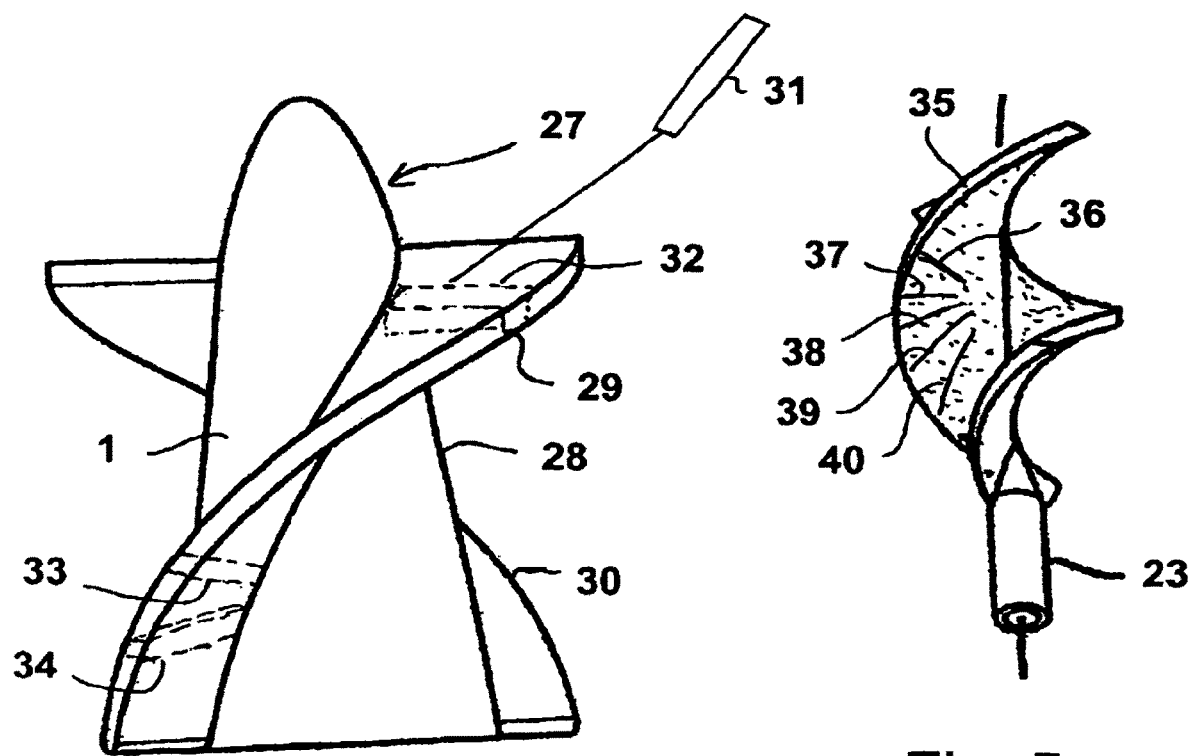
Fig. 4
Fig. 5
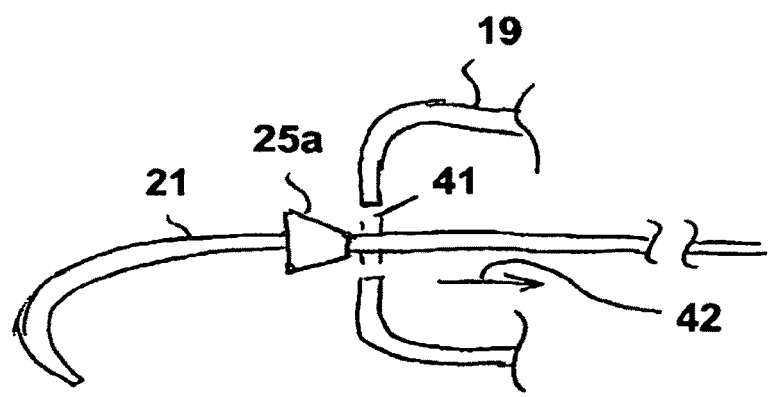
Fig. 6

BLOOD PUMP FOR THE INVASIVE APPLICATION WITHIN A BODY OF A PATIENT

CROSS-REFERENCE TO RELATED APPLICATIONS:

This application is a continuation of U.S. patent application Ser. No. 13/261,563 (allowed), which entered the national stage on Apr. 9, 2013, and which is a United States National Stage filing under 35 U.S.C. § 371 of International Application No. PCT/EP2011/003438, filed Jul. 1, 2011, which claims the benefit of U.S. Provisional Patent Application No. 61/364,595, filed Jul. 15, 2010, and European Patent Application No. 10075304.5, filed Jul. 15, 2010, the contents of all of which are incorporated by reference herein in their entirety. International Application No. PCT/EP2011/003438 was published under PCT Article 21(2) in English.

The invention is in the field of mechanical engineering, in particular micromechanics, and specifically relates to blood pumps.

U.S. provisional application Ser. No. 61/364,559, U.S. provisional application Ser. No. 61/364,595, and U.S. provisional application Ser. No. 61/364,578 are hereby incorporated by reference.

The use of the invention is in particular in the medical field where corresponding blood pumps have already become known in different designs for different purposes. Such pumps can be used invasively and can for this purpose be introduced via a blood vessel into the body of a patient and can be operated there. Such pumps can be used particularly advantageously, for example, in a cardiac chamber, especially in a left ventricle, to assist the heart. Such a pump is for this purpose pushed in via a femoral artery by means of a hollow catheter and is introduced up to and into the left ventricle of a patient's heart. The blood pump there sucks in blood and expels it again in the aorta. In this manner, the heart's function can be replaced at least in part or can be assisted in order, for example, to relieve the heart in surgical procedures in this manner or to improve the conditions for a recovery of the patient's heart.

Such a pump has a drive which can, for example, be disposed outside the patient's body and the drive motion is transferred from said drive through the hollow catheter to the rotor by means of a rotatable shaft. However, the operation of microturbines in the proximity of the blood pump is also known for its drive.

A problem in the efficiency of such pumps is represented by the small dimensions which are advantageous for the transport within the patient's body. Such a pump or the rotor is usually radially compressible for the transport in order then to be expanded for the actual operation.

Various constructions have become known which allow a change of the rotor between a compressed state and an expanded state. Constructions are, for example, known having support struts made from memory alloys which change their shape in dependence on the environmental temperature. The support structures can then be spanned by a membrane to form the impeller blades of a rotor.

Single-part rotors with hubs are also known to which impeller blades are fastened in one piece which can be folded onto the hub and spread apart from it due to their balanced elastic properties. The compression of the impeller blades often takes place by the housing which surrounds the rotor and can be enlarged for the expansion. The erection of the impeller blades can take place, for example, by the rotation of the rotor in operation in that the impeller blades are erected by the arising fluid counter-pressure on the rotation.

A problem in the construction of such blood pumps is, for example, that the demands on the material properties of the material from which the rotor or especially the impeller blades are made are very high. The impeller blades have to be deformed a great deal in locally bounded regions for the complete folding onto the hub, and it is also desirable that the compression forces required for the compression remain small to be able to compress the rotor without any great effort and without any excessive wear. Composite materials have been proposed for this purpose for manufacturing the impeller blades.

On the one hand, they provide an impeller blade body made from a relatively elastic material and on the other hand additional struts which can be integrated into an impeller blade body or which can be placed onto it and which stabilize and support the impeller blade at least in the expanded state.

Various proposals have already become known for a sensible expansion of both the rotor and of the housing surrounding it, such as, for example, the proposal also to expand the housing by the expansion of the rotor or to expand the housing independently of the rotor and thereby to allow the elastic forces acting in the rotor to work which at least partly expand the impeller blades automatically.

Corresponding constructions have become known, for example, from WO 03/103745 and WO 94/05347. It is also proposed there, for example, to apply longitudinal forces to the housing in order to compress it axially, for example, as part of a puling movement, and thus to expand it radially.

It is the underlying object of the present invention to design a blood pump of the initially named kind on the basis of the background of the prior art such that a good compression, as free of forces as possible, of a rotor and/or of the housing of a blood pump is made possible with a construction effort which is as small as possible, with the rotor being stabilized as much as possible in the desired geometrical shape in the expanded state.

The object is satisfied by the features of the independent claims.

A blood pump is accordingly provided for the realization of the invention which has a rotor which can be driven about its axis of rotation and is radially compressible and expandable to be transported through the blood vessel in the compressed state.

In addition, the rotor has a hub and at least one impeller blade fastened thereto and a housing which can be compressed or expanded in the radial direction by an axial stretching or axial compression.

A control body is moreover provided which passes through the hub in the longitudinal direction and which is coupled to the housing on the distal side of the rotor such that it exerts pulling forces and/or compression forces on the housing by a movement in the longitudinal direction with respect to said housing. The control body can preferably be axially displaceable relative to the hub.

Although it is generally known to compress and/or expand corresponding pump housings by exertion of axial forces, no movement or force transmission by the rotor or by the hub itself is required for this purpose with the present invention. An actuation by a control body which passes through the hub can rather take place. Said control body can either rotate with the rotor or be rotationally stationary with respect to it. The control body can, for example, be a guide wire which is introduced into a patient's body before the pump and via which the pump can be pushed to the deployment site.

The control body is freely displaceable in the hub, that is with respect to all parts of the hub. This means that no interaction with the hub occurs on an axial displacement. The pump housing is axially compressed or stretched and thus radially expanded or compressed by actuation of the control body. The rotor has conveying elements which advantageously project radially from the hub and which are radially elastically compressible and are ideally automatically erected on the radial expansion of the housing, in particular exclusively by elastic forces.

The control body can, for example, extend in a hollow drive shaft which is coupled to the hub of the rotor and advantageously also fixes it in the axial direction.

The rotor can also be pushed into the housing in the distal direction after the expansion of the pump housing independently of the control body in the axial direction.

The conveying elements, preferably in the form of conveying blades, are preferably shaped so that they are erected further radially from a position unfolded in a force-free manner in operation to adopt the ideal hemodynamic shape in this position. On a longitudinal stretching of the housing and a corresponding radial compression, the conveying elements can hereby also be compressed.

The control body can be axially displaceably connected to the housing, in particular to its distal end, at the join position. In this respect, the control body can be rotatably supported in the hosing wall.

Provision can advantageously be made that the control body has an abutment body on the distal side of the housing wall, with said abutment body exerting an axial compression force onto the housing wall and thus radially expanding the housing on a pulling movement in the proximal direction.

Provision can additionally or alternatively also be made for this purpose that the control body has an abutment body on the proximal side of the housing wall, with said abutment body exerting an axial expansion force onto the housing wall on a pushing movement in the distal direction.

The corresponding abutment bodies should merely be larger than the bore in the housing wall which passes through the control body. The abutment bodies can also be fastened to the guide body such that they are displaceable lengthways on the control body on application of a specific minimum force. Too great a compression or expansion of the housing is thereby prevented.

Provision can also be made that the abutment bodies can be pressed through the bore in the wall of the pump housing on the exceeding of a specific force threshold, for example when the guide body should be finally removed. Provision can, for example, be made for this purpose that the abutment bodies comprise a compressible material such as foam.

Provision can also be made that the abutment body arranged distal or proximal to the housing wall is dissoluble or deformation such that the control body can be removed. This embodiment can also allow the final removal of the guide body despite the abutment bodies.

The housing of the pump can advantageously have a movable grid mesh simultaneously to produce an expansion or compression in the radial direction by a compression or expansion in the longitudinal direction.

The grid can, for example, have a structure of grid bars which are arranged at least partly helically about the axis of rotation.

The housing can have a membrane supported by the grid mesh for the sealing of said housing. The membrane can be molded with the grid mesh. The grid mesh can also be molded around by an injection molding material.

A further embodiment of the invention relates in accordance with claim 7 to a blood pump for the invasive application within the body of a patient having a housing and a rotor which is arranged in said housing in operation, which is drivable about an axis of rotation and has at least one impeller blade, with the rotor and/or the housing being radially compressible and expandable, characterized in that the rotor and/or the housing at least partly comprises a material which is modified in selected regions with respect to other regions such that it differs from the other regions in the selected regions with respect to at least one mechanical material property such as Young's modulus, the yield strength, the brittleness, elastic stretchability, hardness and/or toughness and/or the Shore hardness.

The selected regions in this respect preferably each extend on only one side of the axis of rotation between a first radial spacing (larger than zero) from the axis of rotation and a larger second radial spacing from the axis of rotation. The first radial spacing is advantageously larger than the radius of the hub if the rotor has a hub. The selected regions thus do not extend radially inwardly up to the axis of rotation or not even up to the hub.

The selected regions can furthermore be free, i.e. not connected to one another, in their parts disposed radially furthest inwardly with respect to the axis of rotation, i.e. close to the axis. This embodiment allows an extremely large freedom of design and permits very large and very free deformations of the rotor, with such designs practically not being able to be manufactured with the aid of prefabricated structures in the form of connected struts or being so unstable that they show unpermitted deformation on the insertion molding, insertion injection or other molding processes. Such selected regions, which are unstable per se, can be introduced into the molded rotor, which serves as a carrier of the selected regions, by the creation and design of the selected regions during or after the molding process.

The selected regions can in extreme cases also all be provided without any mutual connection. The conveying blades can moreover be manufactured with a constant wall thickness since no separate struts have to be insertion molded.

An advantageous embodiment of the invention provides that the selected regions may differ from the other regions by a physical and/or chemical structure. In this respect, the selected regions can differ from the other regions, for example, with respect to their crystalline structure modification, density, the degree of foaming or the chemical cross-linking or other conceivable physical or chemical ordering forces on a molecular or atomic level; the regions can, however, also comprise the same base material in this respect.

The rotor and/or the housing preferably at least partly comprise a material which is modified in selected regions with respect to other regions of the same material with respect to at least one mechanical property. Instead of a modification of the same material, a new material can also arise in the selected regions which, however, belongs to the same class as the starting material. Such classes of materials can be modifications of metals, plastics or kinds of plastic, for example.

The rotor or parts of the rotor are usually first molded in a molding process such as casting, injection, pressing or extrusion. It can then be shaped, bent, stretched, compressed or otherwise treated; it at least has a fixed shape, that is, is solidified, after the shaping.

Provision can be made that the selected regions are modified during the molding process or that the selected regions are modified after the molding process or also that the regions are modified after a first molding process by an additional shaping process.

It can be particularly advantageous in this respect if at least one part of the rotor, in particular an impeller blade, and/or at least one part of the housing comprises a material which can be softened or hardened by radiation and if selected regions are stiffened by selective radiation hardening or if correspondingly selected regions are softened by selective radiation softening. It is generally conceivable in this respect that the material in the selected regions can be modified by radiation, in particular by alpha radiation, beta radiation or gamma radiation and/or by thermal radiation. Mechanical support structures in the form of selected regions can be inscribed into the material of the rotor and/or of the housing in this manner by means of focusable radiation.

The selected regions can already be produced by special casting processes, injection molding processes or extrusion processes in molding processing during shaping. Application processes or immersion processes are also conceivable in which layer grows on layer and in so doing, for example, substance concentrations, solvent concentrations or composition ratios are changed, for example. It is also possible to produce these structures by drop-wise application of the material, with the composition being able to be varied drop-wise.

The selected regions can, however, also only be correspondingly treated after the shaping process, i.e. when the rotor has its final later shape, to change the material directly.

The impeller blade or blades substantially comprise(s) a deformable material, in particular an elastic material, which is easily deformable for the compression of the rotor. High demands on the mechanical stability are, however, made thereon in the elongated position in rotation/pump operation. These demands can be satisfied by a combination of different materials such as a yielding, flexible material and a strut of a harder material as a composite component.

A particularly simple embodiment of such a composite component is provided by the invention in that the impeller blade body comprises a material hardenable or softenable by radiation and selected regions of the impeller blade are selectively hardened as supporting structures or other regions are softened.

Corresponding radiation sources can be sufficiently focused to treat the regions to be hardened accordingly in a selective and delineable manner.

The supporting structures/selected regions are advantageously made as struts which extend within the impeller blade from a point close to the axis of rotation to a point remote from the axis of rotation.

The struts can extend directly in the radial direction or also be inclined at an angle toward the longitudinal axis of the rotor. They can extend from the hub up to the outer end of the impeller blade or over a part distance of this spacing. A meandering or zig-zag extent of the struts is also possible which support the compression of the rotor by forming suitable bending zones.

Such regions formed as struts can, for example, be formed in the housing in the peripheral direction, in the longitudinal direction parallel to the axis of rotation or also running helically about the axis of rotation.

Different struts can be designed parallel to one another, but also in beam form running apart from one another. The force lines of the forces acting under load in an impeller blade can be modeled by the struts. In this case, a plurality of struts can run apart from one another in beam form, for example, from one point or one region.

Provision can also advantageously be made that transition regions which have a smaller degree of hardness than the hardened structures and a higher degree of hardening than the non-hardened regions are provided between the hardened support structures and the non-hardened regions of the impeller blade or of the housing.

The hardening of the support structures subsequently after manufacture of the impeller blade body or of the housing provides the possibility of producing a gradual material transition between a yielding material and a hardened material within the impeller blade body.

The hardened regions can, for example, be arranged at the surface and also only be arranged at the surface of the impeller blade or of the housing or they can lie deep in the interior of the impeller blade or of the housing.

Whole part surfaces within the impeller blades or housing can also be hardened as supporting structures, such as circular or oval plates which can have an extremely stable shape of a spherical cap as required, for example.

The invention also relates, in addition to a blood pump of the above-named kind having the stated advantageous further developments, to a method of manufacturing a blood pump in which the rotor, in particular an impeller blade and/or the housing, is manufactured inhomogeneously in shaping by means of a injection process, an injection molding process or an extrusion process or an application process and/or is modified with respect to mechanical material properties after shaping by radiation in selected regions.

Figure 2:
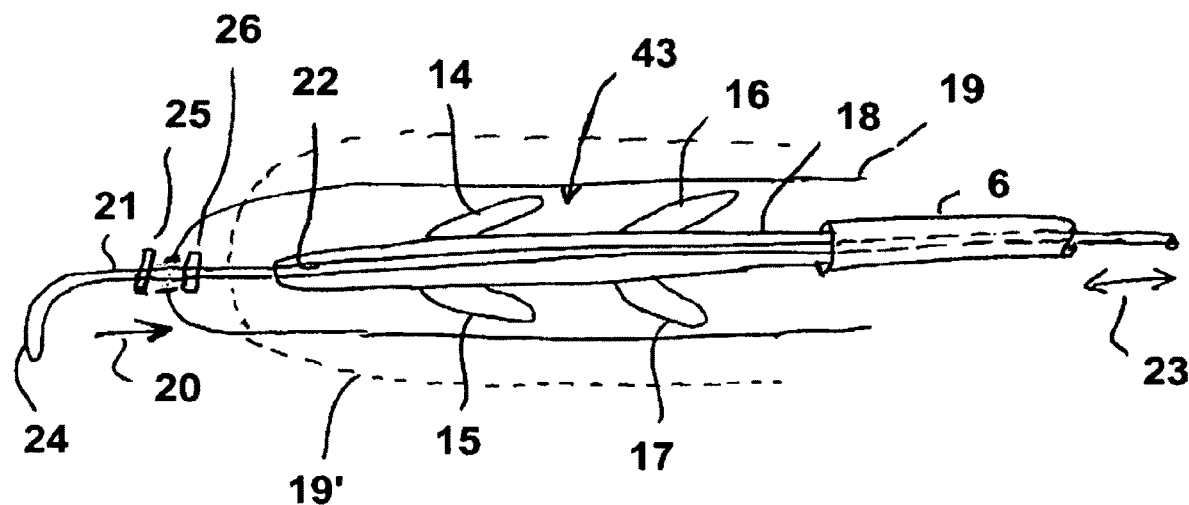
Figure 3:
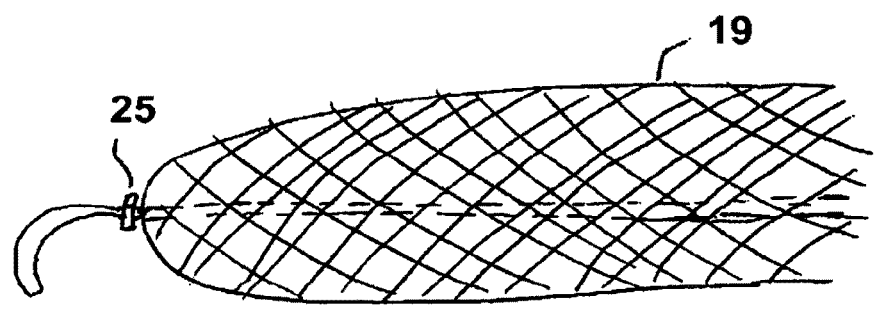

The invention will be shown and subsequently described in the following with reference to an embodiment in a drawing. There are shown FIG. 1 schematically, in an overview, a heart catheter pump which is inserted at least partly into a ventricle;

FIG. 2 in a longitudinal section, the structure of a pump with a rotor and a housing;

FIG. 3 the housing of a pump;

FIG. 4 in a three-dimensional view, a rotor of a pump with a hub;

FIG. 5 in a three-dimensional view, a hubless rotor;

FIG. 6 a detail from a longitudinal section through a pump housing; and

Figure 7:
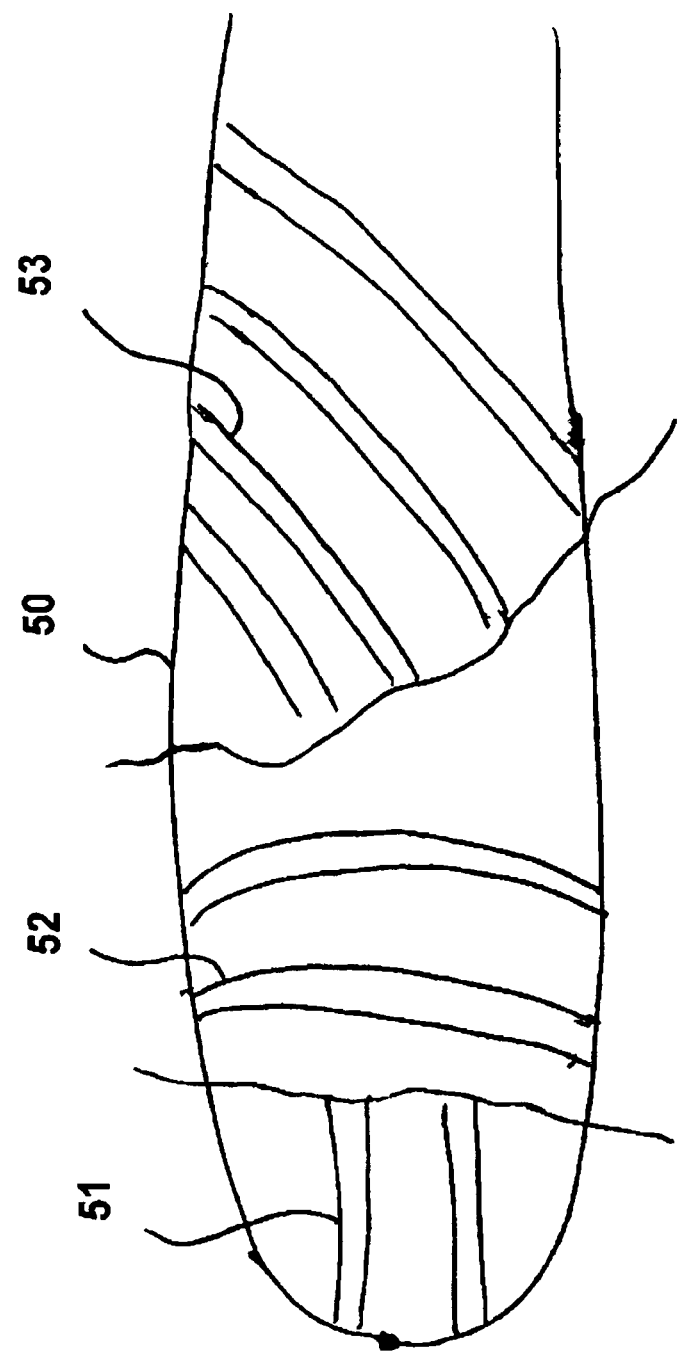

FIG. 7 a housing of a pump reinforced by different types of struts.

FIG. 1 shows a pump 1 which projects into a ventricle 2 of a human heart which is only shown schematically. The pump 1 has a suction cage 3 which leaves openings free for sucking in blood. The inflowing blood is symbolized by the arrows 4, 5.

A rotor is provided within the pump 1, said rotor rotating at a speed between 3000 and 50,000 r.p.m. and conveying the blood into the blood vessel 13 in the longitudinal direction. For this purpose, an outflow hose is pushed over the pump which has outflow openings 10 proximal to the heart valve through which the blood flows off in the direction of the arrows 11. The pump 1 is held at the end of a hollow catheter 6 which is introduced through a sluice 8 into the body of a patient and is there directly introduced into a blood vessel 13. A drive shaft 7 is guided within the hollow catheter 6 and is connected outside the body to a motor 9 and in the pump 1 to a rotor.

FIG. 2 shows the inner structure of the pump 1 in a more detailed representation. A housing 19 is shown in whose interior a rotor 43 is arranged. The rotor 43 has a central hub 18 to which impeller blades 14, 15, 16, 17 are fastened.

To make the rotor radially compressible and expandable, the impeller blades 14, 15, 16, 17 can be laid radially onto the hub 18 to reduce the radius of the pump. The housing 19 is also compressed in its radius in this state.

The impeller blades as well as optionally the hub 18 advantageously comprise an elastic, yielding material which can, however, be reinforced by struts or supports so that the impeller blades can be folded tightly onto the hub due to the yielding, on the one hand, but can remain erected up to the full radial extent, on the other hand.

The impeller blades 14, 15, 16, 17 are usually erected up to and into the expanded state by the putting into operation of the rotor on rotation as a consequence of the fluid counter-pressure which occurs and/or as a consequence of the centrifugal forces. Alternatively to this, or additionally, struts or a framework of a memory material such as nitinol can also be provided which erect the impeller blades on the transition into the expanded state. The housing 19 can also be expanded into the shape 19' shown in FIG. 2 by dashed lines due to this during the erection of the impeller blades.

To facilitate this procedure and to utilize another mechanism for the radial expansion of the housing 19, a control body 21 is provided in accordance with the invention which is formed as a guide wire in the example shown, which passes centrally through an opening 22 in the hub 18 and projects through the wall of the housing 19 to distal at its distal end.

The control body projects through the hub 18 and the hollow catheter 6 and can be actuated, i.e. can be displaced in the longitudinal direction, from outside the body. The control body has a first abutment body 25 distal from the wall of the housing 19 and a second control body 26 proximal to the wall of the housing 19, with the abutment bodies 25, 26 having an at least partially larger radial extent than the opening in the housing 19 which is passed through.

If the control body 21 is retracted in the direction of the arrow 20, that is, in the proximal direction, the housing 19 is thus pressurized in the axial direction and pushed together. Since the housing 19 comprises a movable mesh, for example a wire mesh or a mesh of fibers with a partially helical extent, it is automatically radially expanded on such an axial compression.

The housing is thus moved into the expanded form in which it provides sufficient space for the rotation for the expanded impeller blades.

Fluid can thus accordingly be conveyed within the housing in the axial direction by the impeller blades 14, 15, 16, 17.

The abutment body 25 can be designed such that it first effects an axial compression of the housing 19 on a retraction in the direction of the arrow 42 in FIG. 6, but, on a subsequent larger application of force, is pulled into the recess 41 of the housing 19 due to the conical shape and can be pulled through the opening 41 on a further increase in the axial force. This can be assisted in that the body 25 comprises an at least partially yielding material, for example a foam.

The abutment bodies can also comprise a material, for example, which dissolves in bodily fluids, in particular blood, over time so that the control body can be removed without problems after it has satisfied its function of compression or expansion of the housing 19.

The second abutment body 26 can be utilized correspondingly to the abutment body 25 for an axial expansion of the housing 19 in that the control body 21 is pushed in the opposite direction to the arrow 20 in FIG. 2 and thus an axial expansion force is exerted onto the housing. Within the course of this axial expansion, the housing 19 simultaneously undergoes a radial compression, in the course of which a radial compressive force is also exerted onto the impeller blades 14, 15, 16, 17 so that they are additionally compressed.

In the example shown, the rotor 18 can rotate freely relative to the control body 21 so that the control body 21 is made fixed relative to the rotor with respect to the rotation.

The control body 21 can alternatively to the example shown in the Figures also serve the rotational journalling of the rotor 43 at the distal end of the housing 19.

For this purpose, the control body 21 can be non-displaceably connected to the housing 19 and can be journalled in an axially fixed bearing at the housing 19. On the other hand, the rotor, in particular the hub 18, can also be journalled with respect to the control body 21 by a roller element bearing or plain bearing arranged between them.

FIG. 4 shows in a three-dimensional view a rotor 27 of a compressible and expandable blood pump with a hub 28 which carries two impeller blades 29, 30. The impeller blades 29, 30 run helically about the hub 28. The impeller blades and the hub can, for example, comprise the same flexible, in particular elastic, material.

The impeller blades can also be made shorter than shown in the illustration so that a plurality of impeller blades are distributed at the periphery of the hub 28.

Supporting structures 32, 33, 34 in the form of integrated struts which are arranged within the volume of the impeller blade 29 are shown within the impeller blade 29. They are formed in accordance with the invention in that specific regions within the material or a material of the impeller blade 29 are hardened directly and selectively.

For this purpose, the impeller blade 29 at least partially comprises a material which can be hardened by means of radiation, in particular light, UV light, laser radiation, X-rays or alpha radiation, beta radiation or gamma radiation, for example an elastomer having hardenable portions. It can in this respect be a radiation-cross linkable rubber, for example.

A controllable laser 31 is shown by way of example in FIG. 4 by means of which the regions of the support structures can be radiated directly and thus be hardened to the desired degree. The contours of the regions to be hardened can thus be designed as sharp; it is, however, also conceivable to provide gradual transitions between hardened regions and non-hardened regions in which the material is only partially hardened.

The struts can advantageously be arranged in the expanded state in the radial direction of the rotor. The formation of the struts by the radiation hardening can advantageously take place in the force-free state or in the expanded state to achieve the desired shape and alignment of the supporting structures as precisely as possible.

FIG. 5 shows a hubless rotor having an impeller blade 35 into which support structures 36, 37, 38, 39, 40 in the form of struts extending in beam shape are introduced by selective solidification.

FIG. 7 shows selected hardened regions at a housing 50 for the example of struts 51 extending parallel to the axis of rotation, struts 52 extending in the peripheral direction and struts 53 running around helically.

The formation of the support structures by means of a controllable irradiation also has the advantage with respect to the introduction of prefabricated fixed structures that very complex geometrical forms can be produced as support structures. In addition, an insertion molding of struts using an injection molding material, with the struts being able to be deformed or displaced by the application of force in dependence on the viscosity of the injection molding material, is dispensed with.

Thanks to the design of various elements of the pump, the invention allows a comfortable compression or expansion of the pump, together with an optimized stability in the expanded state and a good and reversible compressibility of the impeller blades.

Aspects of the invention are inter alia:

1. A blood pump for the invasive application within a body of a patient comprising a rotor (43, 27) which is drivable about an axis of rotation, which is radially compressible and expandable and which has a hub (18, 28) and at least one impeller blade (14, 15, 16, 17, 29, 30) fastened thereto as well as comprising a housing (19, 19') which is compressible or expandable in the radial direction by a axial stretching or axial compression, characterized in that a control body (21) passing through the hub (18) in the longitudinal direction is provided which is coupled to the housing on the distal side of the rotor such that it exerts pulling and/or compression forces onto the housing by a movement in the longitudinal direction with respect to the housing.
2. A blood pump in accordance with aspect 1, characterized in that the control body (21) rotates with the rotor (18).
3. A blood pump in accordance with aspect 1, characterized in that the control body (21) is stationary with respect to the rotor (18).
4. A blood pump in accordance with aspect 1 or one of the following aspects, characterized in that the control body (21) is axially non-displaceably connected to the housing (19, 19').
5. A blood pump in accordance with aspect 1, aspect 2 or aspect 3, characterized in that the control body (21) passes through the housing wall and has at its distal side an abutment body (25) which exerts a compressive force in the axial direction onto the housing on the retraction of the control body in the proximal direction.
6. A blood pump in accordance with one of the aspects 1, 2, 3 or 5, characterized in that the control body (21) has an abutment body (26) on the proximal side of the housing wall, said abutment body exerting an axial expansion force onto the housing wall on a pushing movement in the distal direction.
7. A blood pump in accordance with aspect 1 or one of the following aspects, characterized in that the control body (21) is made as a guide wire.
8. A blood pump in accordance with aspect 1 or one of the following aspects, characterized in that the abutment body (25, 26) arranged distal or proximal to the housing wall can be dissolved or deformed such that the control body can be removed.
9. A blood pump in accordance with aspect 1 or one of the following aspects, characterized in that the housing (19, 19') has a movable grid mesh.
10. A blood pump in accordance with aspect 9, characterized in that the housing (19, 19') has a membrane supported by the grid mesh.
11. A blood pump for the invasive application within the body of a patient comprising a housing as well as a rotor (43, 27) which is arranged in said housing in operation and has at least one impeller blade (14, 15, 16, 17, 29, 30, 35), wherein the rotor and/or the housing (19, 19') is/are radially compressible and expandable, characterized in that the rotor and/or the housing comprise(s) at least partially a material which is modified in selected regions (32, 33, 34, 36, 37, 38, 39, 40) with respect to other regions such that it differs from the other regions with respect to mechanical properties in the selected regions.
12. A blood pump in accordance with aspect 11, characterized in that the selected regions (32, 33, 34, 36, 37, 38, 39, 40) differ from the other regions by a physical and/or chemical structure.
13. A blood pump in accordance with aspect 11 or aspect 12, characterized in that the selected regions (32, 33, 34, 36, 37, 38, 39, 40) are modified during the molding process.
14. A blood pump in accordance with aspect 11 or aspect 12, characterized in that the selected regions (32, 33, 34, 36, 37, 38, 39, 40) are modified after the shaping process.
15. A blood pump in accordance with aspect 11 or one of the following aspects, characterized in that at least a part of the rotor (43, 27), in particular an impeller blade, and/or at least a part of the housing comprise(s) a material which be softened or hardened by radiation; and in that selected regions (32, 33, 34, 36, 37, 38, 39, 40) are stiffened by selective radiation hardening or correspondingly selected regions are softened by selective radiation softening.
16. A blood pump in accordance with aspect 11 or one of the following aspects, characterized in that the material is modified in the selected regions by radiation, in particular by alpha radiation, beta radiation or gamma radiation and/or by thermal radiation.
17. A blood pump in accordance with aspect, 11, aspect 12 or aspect 13, characterized in that stiffened selected regions (32, 33, 34, 36, 37, 38, 39, 40) are struts which extend within the impeller blade (29, 30, 35) from a point close to the axis of rotation to a point remote from the axis of rotation.
18. A blood pump in accordance with aspect 11 or one of the following aspects, characterized in that transition regions which have a lower degree of hardness than the hardened structures and a higher degree of hardness than the non-hardened regions are provided between the hardened support structures (32, 33, 34, 36, 37, 38, 39, 40) and the non-hardened regions of the impeller blade (29, 30, 35) or of the housing.
19. A blood pump in accordance with aspect 11 or one of the following aspects, characterized in that the selected regions, in particular supporting structures, are disposed at the surface of the impeller blade (29, 30, 35) or of the housing.
20. A blood pump in accordance with aspect 11 or one of the following aspects, characterized in that the supporting structures are disposed in the interior of the impeller blade (29, 30, 35).
21. A method of manufacturing a blood pump in accordance with one of the aspects 11 to 20, characterized in that the rotor (43, 27), in particular an impeller blade (14, 15, 16, 17, 29, 30, 35), and/or the housing (19, 19') is/are manufactured inhomogeneously by means of an injection process, an injection molding process or an extrusion process or an application process on the shaping and/or is/are modified with respect to mechanical material properties after the shaping by radiation in selected regions (32, 33, 34, 36, 37, 38, 39, 40).
22. A method in accordance with aspect 21, wherein the injection process is characterized by drop-wise application of the material with variation of the composition of the drops.

The invention claimed is:
1. A blood pump for insertion within a body of a patient comprising:
   a housing; and a rotor arranged in the housing during operation of the rotor, the rotor having at least one impeller blade, the rotor having a first region and a second region, the first region and the second region formed from a same material having a first material state and a second material state;

wherein in the first material state, the material is homogeneous across the first and second regions, and wherein in the second material state, the material is modified in the first region with respect to the second region such that the first region differs from the second region with respect to at least one mechanical property, and wherein the rotor, in the second material state including the modified first region and the second region, is radially compressible and expandable.

2. The blood pump of claim 1, wherein the housing is radially compressible and expandable.

3. The blood pump of claim 1, wherein the first region differs from the second region by a physical modification.

4. The blood pump of claim 1, wherein the first region differs from the second region by a chemical modification.

5. The blood pump of claim 1, wherein the first region is disposed between a first radial spacing from an action of rotation of the rotor and a larger second spacing from the axis of rotation.

6. The blood pump of claim 1, wherein the first region is stiffened by selective radiation hardening.

7. The blood pump of claim 1, wherein the first region is softened by selective radiation softening.

8. The blood pump of claim 1, wherein at least a portion of the first region is hardened for forming support structures which extend within the at least one impeller blade.

9. The blood pump of claim 8, wherein the support structures extend within the impeller blade from a point close to the axis of rotation to a point remote from the axis of rotation.

10. The blood pump of claim 9, wherein the support structures are surrounded by transition regions which have a lower degree of hardness than the support structures and a higher degree of hardness than non-hardened regions.

11. The blood pump of claim 10, wherein the transition regions are provided in the first region between the support structures and the non-hardened regions of the at least one impeller blade.

12. The blood pump of claim 11, wherein the support structures are disposed at a surface of the at least one impeller blade.

13. The blood pump of claim 11, wherein the support structures are disposed in an interior of the at least one impeller blade.

14. The blood pump of claim 11, wherein the support structures comprise supportive struts.

15. The blood pump of claim 14, wherein the impeller blade has a constant thickness.

16. A blood pump for insertion within a body of a patient comprising:

a housing; and a rotor arranged in the housing during operation of the rotor, the rotor having at least one impeller blade;

the housing having a first region and a second region, the first region and the second region formed from a same material having a first material state and a second material state;

wherein in the first material state, the material is homogeneous across the first and second regions, and wherein in the second material state, the material is modified in the first region with respect to the second region such that the first differs from the second region with respect to at least one mechanical property, and wherein the housing, in the second material state including the modified first region and the second region, is radially compressible and expandable.

17. The blood pump of claim 16, wherein the first region differs from the second region by a physical modification.

18. The blood pump of claim 16, wherein the first region differs from the second region by a chemical modification.

19. The blood pump of claim 16, wherein at least a portion of the first region is hardened for forming support structures which extend within the housing.

20. The blood pump of claim 19, wherein the support structures are surrounded by transition regions which have a lower degree of hardness than the support structures and a higher degree of hardness than non-hardened regions.

21. The blood pump of claim 1, wherein the material is configured to transition from the first material state to the second material state prior to introduction of the pump into the patient.

* * * * *

UNITED STATES PATENT AND TRADEMARK OFFICE
CERTIFICATE OF CORRECTION

PATENT NO. : 10,589,012 B2
APPLICATION NO. : 15/815931
DATED : March 17, 2020
INVENTOR(S) : Thomas Toellner et al.

It is certified that error appears in the above-identified patent and that said Letters Patent is hereby corrected as shown below:

In the Claims

Column 11, Claim 5, Line 24:
Now reads: "from an action"; should read -- from an axis --

Column 11, Claim 9, Line 36:
Now reads: "close to the"; should read -- close to an --

Column 12, Claim 16, Line 21:
Now reads: "second regions, and"; should read -- second regions, --

Signed and Sealed this
Fifth Day of July, 2022

Katherine Kelly Vidal
*Director of the United States Patent and Trademark Office*